(12) United States Patent
Rathert (10) Patent No.: US 9,610,154 B2
(45) Date of Patent: Apr. 4, 2017

(54) INJECTOR TIP FOR AN OCULAR LENS INJECTOR DEVICE, DEVICE WITH AN INJECTOR TIP AND AN OCULAR LENS, AS WELL AS OCULAR LENS INJECTOR DEVICE

(71) Applicant: Carl Zeiss Meditec AG, Jena (DE)

(72) Inventor: Brian Rathert, Frauenfeld (CH)

(73) Assignee: Carl Zeiss Meditec AG, Jena (DE)

( * ) Notice: Subject to any disclaimer, the term of this patent is extended or adjusted under 35 U.S.C. 154(b) by 234 days.

(21) Appl. No.: 14/359,878

(22) PCT Filed: Nov. 20, 2012

(86) PCT No.: PCT/EP2012/073080
§ 371 (c)(1),
(2) Date: May 21, 2014

(87) PCT Pub. No.: WO2013/076067
PCT Pub. Date: May 30, 2013

(65) Prior Publication Data
US 2015/0018836 A1    Jan. 15, 2015

(30) Foreign Application Priority Data
Nov. 22, 2011  (GB) .................................. 1121372.5

(51) Int. Cl.
*A61F 2/16*    (2006.01)

(52) U.S. Cl.
CPC ............ *A61F 2/167* (2013.01); *A61F 2/1662* (2013.01)

(58) Field of Classification Search
CPC ........................................ A61F 2/1662–2/1678

USPC ........................................................ 606/107
See application file for complete search history.

(56) References Cited

U.S. PATENT DOCUMENTS

| 5,928,245 A | 7/1999 | Wolf et al. |
| 6,712,848 B1 | 3/2004 | Wolf et al. |
| 2003/0050647 A1* | 3/2003 | Brady .................. A61F 2/1664 606/107 |

(Continued)

FOREIGN PATENT DOCUMENTS

| EP | 1262154 A1 | 12/2002 |
| EP | 1290990 A1 | 3/2003 |

(Continued)

OTHER PUBLICATIONS

Merriam-Wester Dictionary, definition of "steep", http://www.merriam-webster.com/dictionary/steep as accessed on Apr. 6, 2016.*

(Continued)

*Primary Examiner* — Todd J Scherbel
(74) *Attorney, Agent, or Firm* — Fitch, Even, Tabin & Flannery LLP (57) ABSTRACT

The invention concerns an injector tip (7) for an ocular lens injector device (1), the injector tip having an injection duct (16) with a front (9) and a rear end (8) and being bounded by an inner wall (17), wherein at the inner wall (17) an inwardly extending step (18) is formed only along part of the entire length between the front (9) and the rear end (8) of the injection duct (16) and ends at a distance from the front end (9) of the injection duct (16). The invention also relates to an ocular lens injector device (1) with an injector tip (7).

15 Claims, 6 Drawing Sheets

(56) References Cited

U.S. PATENT DOCUMENTS

2005/0075646 A1    4/2005   Ohno et al.
2011/0144653 A1    6/2011   Pankin et al.

FOREIGN PATENT DOCUMENTS

| EP | 2161004 A1 | 3/2010 |
| --- | --- | --- |
| EP | 2161006 A1 | 3/2010 |
| EP | 2368526 A1 | 9/2011 |

OTHER PUBLICATIONS

Merriam-Wester Dictionary, definition of "flat", http://www.merriam-webster.com/dictionary/flat as accessed on Apr. 6, 2016.*
International Search Report and Written Opinion, International Patent Application No. PCT/EP2012/073080, dated Feb. 21, 2013, 13 pages.
Great Britain Search Report, British Application No. 1121372.5, dated Mar. 8, 2012, 1 page.

* cited by examiner

INJECTOR TIP FOR AN OCULAR LENS INJECTOR DEVICE, DEVICE WITH AN INJECTOR TIP AND AN OCULAR LENS, AS WELL AS OCULAR LENS INJECTOR DEVICE

CROSS REFERENCE TO RELATED APPLICATIONS

This application is a national phase application of International Application No. PCT/EP2012/073080, filed Nov. 20, 2012, designating the United States and claiming priority to British Patent Application No. 1121372.5, filed Nov. 22, 2011, both of which are incorporated by reference herein in their entireties.

TECHNICAL FIELD

The invention concerns an injector tip for an ocular lens injector device, the injector tip having an injection duct having a front and a rear end and being bounded by an inner wall. At the inner wall an inwardly extending step is formed. Moreover, the invention concerns a device having such an injector tip and an ocular lens, in particular an intraocular lens. Furthermore, the invention also concerns an ocular lens injector device with an injector tip.

PRIOR ART

Intraocular lenses are implanted as implants into an eye and replace the natural lens. For this purpose injector devices are provided which have a plunger that is guided within an injector tube. At the front end of the injector tube is a reception space for the intraocular lens, wherein this reception space can be formed in a separate cassette, which is insertable into a frame of the injector tube. It may also be provided that this reception space for the intraocular lens is integrally formed within the injector tube. Moreover, an injector tip is formed adjacent to the reception space towards the front, the injector tip having a guide duct, through which the intraocular lens upon being ejected from the reception space is pushed and which it exits in a folded state towards the front to be inserted into the eye. The front side of the tip is directly introduced into the eye.

In known intraocular lenses with common known injector tips and injector devices the problem arises that they with regard to their folding they either roll up uncoordinatedly, so that particularly in the case of asymmetrical lenses having an optical element with differently curved surfaces, possibly the folding occurs in an undesired incorrect direction.

The folding can occur in different ways. The intraocular lens in this connection is rolled up into an injector tip which commonly tapers conically with its inner wall towards the front.

This is known for instance from the EP 1 290 990 B1. Therein it is envisaged that at an inner wall of the injector tip along the entire length of the inner wall an inwardly extending step is formed. Moreover, this step is formed inwardly extending with a constant height along the entire length, which means that along its entire length and thus viewed in the direction of the longitudinal axis of the injector tip it has the same distance from this longitudinal axis. Moreover, the step formation shown therein viewed in the circulation direction about this longitudinal axis is extremely compact and concentrated in one place and in the cross-section has an either rectangular or slightly triangular, asymmetrical design. The inner wall except for the very small and minimal section of the step, if viewed in the circulation direction, has a constant radius. Moreover, at the transition of the radius of the inner wall to the step bends or edges are formed.

Through the known design of the injector tip the folding or rolling of the intraocular lens involves numerous problems. In that this step extends along the entire length of the injector tip, a movement hindrance to the intraocular lens is created particularly when the intraocular lens exits from the injector tip. Through the very discrete step design with the bends the roll-up process of the intraocular lens is moreover impeded and cannot take place in a continuously sliding manner. The edges of the intraocular lens thereby may get caught in these bends and then can only abruptly free themselves from this position, if a correspondingly larger force acts upon them. This may lead to damages to the intraocular lens. Equally, undesired foldings of the intraocular lens may occur, which in the course of the further ejection process continue to exist and cannot be removed anymore. The folding of the lens through the step formation thus is performed very abruptly. In particular by this design of the step, as it is named in this prior art, also a very strong bending or folding at the edge of the intraocular lens is performed, so that very locally undesired strong bends of the lens occur, which may lead to mechanical tensions and excessive stresses of the lens material.

DESCRIPTION OF THE INVENTION

It is the task of the present invention to provide an injector tip for an ocular lens injector device, and a device with such injector tip and an ocular lens, by means of which the folding of the lens with regard to an overlapping of the lens edges can be performed continuously and with as little mechanical stress as possible exerted upon the ocular lens.

This task is solved by an injector tip, a device, and an ocular lens injector device according to the independent claims.

According to the invention an injector tip for an ocular lens injector device comprises an injection duct having a front and a rear end. The injection duct is bounded by an inner wall, wherein at the inner wall an inwardly extending step is formed. The step is formed only partly, or in other words along part of the entire length, between the front and the rear end of the injection duct and is formed to end at a distance from the front end of the injection duct. The step thus does not extend along the entire length of the injection duct, but is shorter. Through such design particularly the exiting behaviour of the folded lens is clearly improved. The injection duct is designed in particular such that it conically tapers from the rear end to the front end. With the named design of the step according to the invention in this connection a very continuous and stress-free folding of the lens immediately upon entry into the injection duct can be facilitated, which sufficiently occurs in particular with regard to the overlapping of the edges of the intraocular lens in front of the front end of the injection duct, and the further folding can then also take place without this step.

Preferably, it is provided that the step is formed to end in the rear end of the injection duct. This is advantageous, since immediately upon entry of the intraocular lens into the injection duct the folding of the lens is supported and in a very continuous further process the overlapping of the edges of the intraocular lens during this folding or rolling-up is specifically supported. This helps to avoid a collision of edges and an abrupt rolling-up or a short-term mechanical excessive application of force to the lens for the further rolling-up.

Preferably, it is envisaged that the step at least partly along the length of its crown line has a non-straight course of the crown line. The crown line in this connection represents the line which reflects the maximum height of the outline at the level of the step or the ridge of a formation which then slopes towards both sides. With regard to this non-straight course the distance from a central longitudinal axis of the injection duct is provided. The distance of this crown line from this central longitudinal axis thus varies at least once along the entire length. Such shape of the step is particularly advantageous with regard to the continuous, smooth rolling-up of the intraocular lens within the injector tip, which moreover can occur even without applying short-term undesired large force peaks to the intraocular lens.

The crown line represents a gradient of an elevation, wherein the elevation viewed in the circulation direction about the central longitudinal axis of the injector tip slopes on both sides.

Preferably, it is envisaged that the crown line has a rising first crown line section and a falling second crown line section. This is based on a perspective view from the rear end of the injection duct into the direction of the front end. This means that thus the step viewed from the rear end of the injection duct, to start with, has a rising crown line section. This is particularly advantageous to the effect that thus upon entry of the intraocular lens into the injection duct a very smooth rolling-up behaviour of the intraocular lens can be achieved and the edges are not faced with an abrupt and a very high step already at the beginning of the rolling-up process.

The rising and the falling of the crown line sections occur gradually at a specific inclination.

Corresponding advantages are also achieved at the end of the step with the falling second crown line section.

Preferably, it is envisaged that the crown line has a straight third crown line section. The crown line thus in this third crown line section has a constant distance from the central longitudinal axis of the injector tip or the injection duct. Such trapezoidal cross-sectional design of the step particularly supports the rolling-up behaviour by involving the advantages as already set out in the above.

Preferably, it is envisaged that the height of the third crown line section also forms the maximum height of the step.

Insofar it is provided that the height of the third crown line section amounts to between 0.1 mm and 0.4 mm, in particular between 0.15 mm and 0.25 mm. The height is measured from the inner wall in the direction of the central longitudinal axis.

Preferably, the length of the third crown line section and thus the extension in the direction of the longitudinal axis of the injector tip is between 1 mm and 3 mm, preferably between 1.5 mm and 2.5 mm.

In particular it is envisaged that the third crown line section is shorter than the second crown line section. Preferably it is envisaged that the second crown line section is between 1.5 times and 5 times the length of the third crown line section, preferably between 2.5 times and 3.5 times the length of the third crown line section.

Preferably, it is also envisaged that the third crown line section in the direction of the longitudinal axis of the injector tip and thus also of the injection duct is shorter than first crown line section. In particular it is envisaged that the first crown line section is larger than the third crown line section and smaller than 2.5 times the third crown line section.

Preferably, the third crown line section is shorter than the first crown line section and also shorter than the second crown line section. In particular it is envisaged that the second crown line section viewed in the direction of the longitudinal axis of the injector tip is longer than the first crown line section, in particular amounts to between 1.5 times and 3 times the length of the first crown line section.

Preferably it is provided that the third crown line section is formed between the first and the second crown line sections.

In particular the step is formed at least along the length of the first and the third crown line sections in the rear half—starting from the rear end of the of the injector tip—of the length of the injector tip. In particular also at least half of the section of the step with the second crown line section is formed in the rear half of the length of the injector tip.

Preferably the overall length of the step amounts to a maximum of three quarters, in particular maximum of two thirds, of the length of the injector tip.

Preferably, the front end of the step is formed offset backwards by a length of one quarter and one third of the length of the injector tip relative to the front end of the injector tip.

Preferably, it is envisaged that the step in the circular direction about a central longitudinal axis of the injection duct has a steep step flank and a flat step flank, which converge at the crown line.

It is particularly advantageous, if the flat step flank has a curved outline extending from the step up to an inner wall place, which in the circulation direction about the central longitudinal axis of the injection duct is at a distance from the step at an angle of between 70° and 190°. Through such design a continuous and steadily curved flat step flank is created, which moreover extends very far across the entire length of the outline of the inner wall in this circulation direction about the central longitudinal axis. Through this specific curvature the flat step flank and moreover this long extension in the circulation direction a steep abrupt ramp of the step can be avoided and a particularly continuous smooth rolling-up of this intraocular lens avoiding force peaks applied to the intraocular lens can be achieved. Particularly in connection with the non-straight course of the crown line of the step thereby a particularly advantageous folding and thus rolling-up of the intraocular lens in the injector tip is achieved.

Preferably, it is envisaged that the flat step flank has a small second radius, which corresponds to the radius of the inner wall from the crown line up to an inner wall place, which is at a distance from the step at an angle of between 70° and 190° in the circulation direction about the central longitudinal axis of the injection duct. Through this specification the second step flank is of an entirely individual continuously curved design. In particular it can be provided that this inner wall place is formed at an angle of between 70° and 100°, at a distance from the step, in particular a crown line of the step. In an alternative embodiment it can be envisaged that this inner wall place is formed at an angle of 170° and 190° viewed in the circulation direction, at a distance from the step, in particular the crown line. As a first approximation it thus can be envisaged that the flat step flank in a first embodiment extends across about a quarter of the entire circumferential inner wall outline. In a second embodiment it can be envisaged that this flat step flank extends along about half of the circumferential inner wall outline.

Preferably, it is envisaged that the inner wall in a cross-section perpendicularly to a central longitudinal axis of the injection duct has a first wall section with a first radius, which extends from a first step flank end of a steep step flank of the step up to an inner wall place with the first radius, wherein the inner wall place starting from the step in the direction of the first wall section is formed at an angle of between 150° and 290°, in particular between 170° and 280°, at a distance from the step. This means that it is envisaged that the outline of the inner wall in the cross-section is formed such that it approximately extends along three quarters of the circumference at the same first radius.

Preferably, it is envisaged that the inner wall in the cross-section in which the first radius in the above embodiment is formed, is designed with a second radius which is smaller than the first radius, which extends from the second step flank end of a flat step flank up to the inner wall place. The step in this embodiment is quasi formed by two circular arcs, which have different radii, wherein the circular arcs intersect and converge in a first point, namely the inner wall place, to the effect that they share the same tangent at this inner wall place. At the respective other ends of these arcs or circle segment sections due to the different radii then the step is formed.

With regard to the angle indication, with respect to which the inner wall place is formed at a distance from the step starting from the step in the direction of the first wall section, thus the most varied embodiments of the outline of the inner wall can be provided.

Preferably, it is provided that the inner wall place starting from the step in the direction of the first wall section at an angle of between 170° to 190°, or in an alternative embodiment at an angle of between 260° and 290°.

Preferably, it is provided that the flat step flank ending in the inner wall place at the inner wall place has the same tangent as the wall section ending from the other side in the inner wall place. Viewed in the circulation direction about the central longitudinal axis, thus at this inner wall place a continuous transition without bends is formed between the flat step flank and the other wall section of the inner wall.

The explanations given for a cross-sectional view according to claims 7 to 11 apply in particular if viewed in the longitudinal direction of the step to at least one third of, in particular at least half of, in particular at least three quarters of, and in particular the entire length of the step.

Preferably, it is envisaged that the position of a maximum height of a crown line of the step in the direction of the central longitudinal axis starting from the rear end of the injection duct is dependent on the inner diameter Di of the injection duct and the diameter D0 of an optical element of an intraocular lens, which is to be slid through the injector tip, and the thickness E0 of this intraocular lens at the edge. In particular in this connection the relationship $Di=(1/\pi)*D0+E0$ applies.

Preferably it is envisaged that the maximum height of the step at the crown line amounts to between >0.5 E0 and <E0. For instance this maximum height may amount to between 0.04 mm and 0.5 mm.

In particular the position of this maximum height and thus preferably in particular also the position of the third crown line section along the longitudinal axis of the injector tip is a parameter to be highlighted with regard to the design of the step and its position. In particular this maximum height of the step is formed at the point of the injector tip, at which the two opposing edges of the intraocular lens come or would come into physical contact during rolling-up. This moment of the possible physical contact occurs in the area along the longitudinal axis of the injector tip and thus in the cross-sectional plane perpendicular to this central longitudinal axis, at which the relationship $Di=(1/\pi)*D0+E0$ already mentioned in the above applies.

For instance it may be envisaged that E0 has values of between 0.1 mm and 0.4 mm. D0 for instance may have values of between 5 mm and 7 mm, in particular between 5.5 mm and 6.5 mm.

It may be envisaged that the maximum height of the step is smaller than or equal to or larger than the thickness of the edges of the intraocular lens. Preferably, it is envisaged that the maximum height is not larger than necessary, so that the desired continuous rolling-up is facilitated with a cross-sectional overlapping of the edge portions of the intraocular lens.

Preferably, it is envisaged that the step relative to a plane that is vertically orientated and has the central longitudinal axis, is arranged at an angle of between 0° and 1°. This means that the step according to an embodiment extends with its crown line in this plane or is positioned at an angle inclined thereto.

A further independent aspect of the invention concerns an injector tip for an ocular lens injector tip, which has an injection duct with a front and a rear end bounded by an inner wall, wherein at the inner wall an inwardly extending step is formed. The step has a crown line with a non-straight course. This means that the distance of the crown line from a central longitudinal axis of the injector tip and thus also the injection duct varies or changes. Additionally or instead, with regard to this aspect of the injector tip it may be provided that a flat step flank of the step viewed in the circulation direction about a central longitudinal axis of the injector tip extends over an angle interval of between 80° and 190°, wherein this angle interval is measured starting from the step, in particular the crown line in the direction of the flat step flank.

Embodiments of this aspect of the invention are to be regarded as advantageous embodiments of the further independent aspect.

Moreover, the invention relates to a device with an injector tip according to the invention or an advantageous embodiment thereof, and an ocular lens, in particular an intraocular lens which in particular is arranged within the injector tip.

Moreover, the invention concerns an ocular lens injector device with an inventive injector tip or an advantageous embodiment thereof, or a device according to the invention.

Further features of the invention derive from the claims, the figures, and the description of the figures. The aforementioned features and feature combinations named in the description and also the features and feature combinations shown in the description of the figures and/or in the figures alone can not only be used in the respective indicated combination but also in any other combination or be taken alone without leaving the scope of the invention.

BRIEF DESCRIPTION OF THE DRAWINGS

Embodiments of the invention are explained in the following in more detail by making reference to the schematic drawings. These show in.

PREFERRED EMBODIMENTS OF THE INVENTION

In the figures same elements or elements with the same functions are equipped with the same reference signs.

Figure 1:
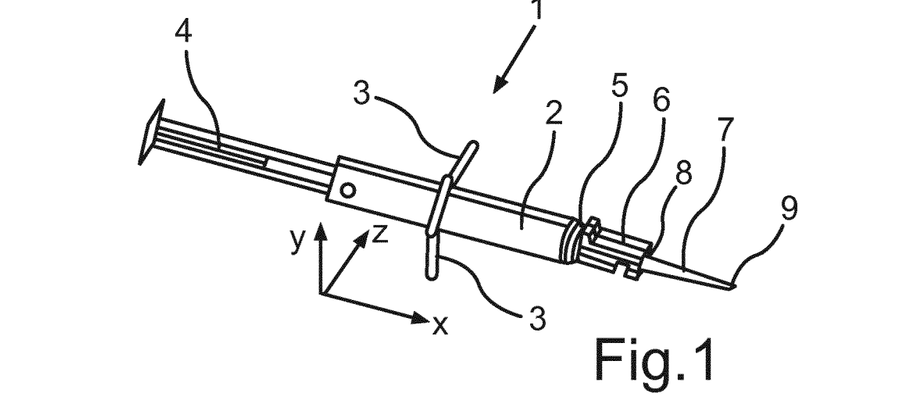
FIG. 1 a schematic perspective view of an embodiment of an ocular lens injector device according to the invention.

In FIG. 1 in a perspective view an embodiment of an ocular lens injector device 1 is shown. By means of this injector device 1 an intraocular lens can be inserted into an eye. The injector device 1 comprises an injector tube 2, at which two gripping lugs 3 are arranged. The injector device 1 moreover comprises a plunger 4, which is shiftable within the injector tube 2 in the x direction in the longitudinal direction, so that by means of this plunger 4 an intraocular lens can be ejected.

At a front end 5 of the injector tube 2 is formed a reception space 6 for a cassette, which is not shown in more detail, within which the intraocular lens is arranged. A cassette can also be integrally formed with the injector tube 2.

Closing off at the front an injector tip 7 is arranged. This can be arranged to be removable from the injector tube 2 or integrally connected with it.

In the embodiment the injector tip 7 with a rear end 8 is arranged adjacent to the frame or the reception space 6. A front end 9 of the injector tip 7 can be inserted into the eye and the lens can be ejected via the front end 9.

Figure 2:
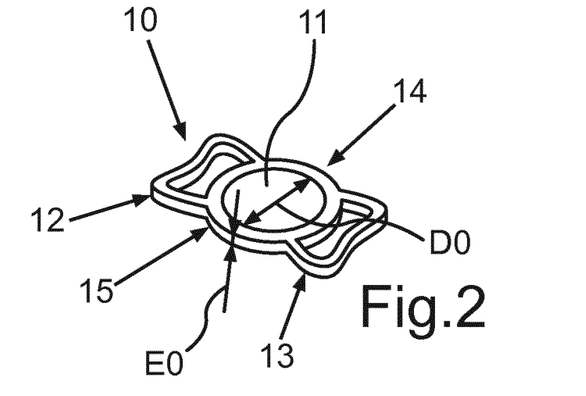
FIG. 2 a perspective view of an embodiment of an intraocular lens.

In FIG. 2 as an example an intraocular lens 10 is shown as ocular lens. This intraocular lens 10 comprises an optical element 11, adjacent to which the opposing haptic elements 12 and 13 are arranged. The haptic elements 12 and 13 each are connected to two ends of the optical element 11. The haptic elements 12 and 13 can also be of a different design and can for instance be C-shaped lugs. The haptic elements 12 and 13 can also have a different design, so that the representation in FIG. 2 of the intraocular lens 10 merely serves for general representation, but in no way is to be understood as restrictive.

The intraocular lens 10 has a thickness E0 at the opposing sides or edges 14 and 15.

Figure 3:
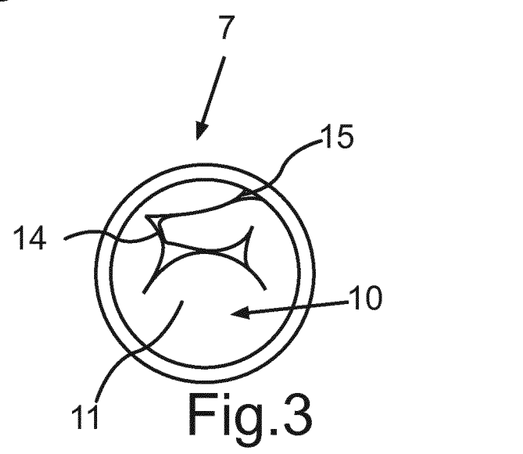
FIG. 3 a cross-sectional view of an injector tip with the intraocular lens according to FIG. 2 in the folded state.

In FIG. 3 in a cross-sectional representation in the y-z plane the injector tip 7 is shown with intraocular lens 10 already arranged and folded therein, the intraocular lens being folded such that the edges 14 and 15 rolled-up into each other or guided in each other and thus are quasi positioned to overlap in the circular direction.

Figure 4:
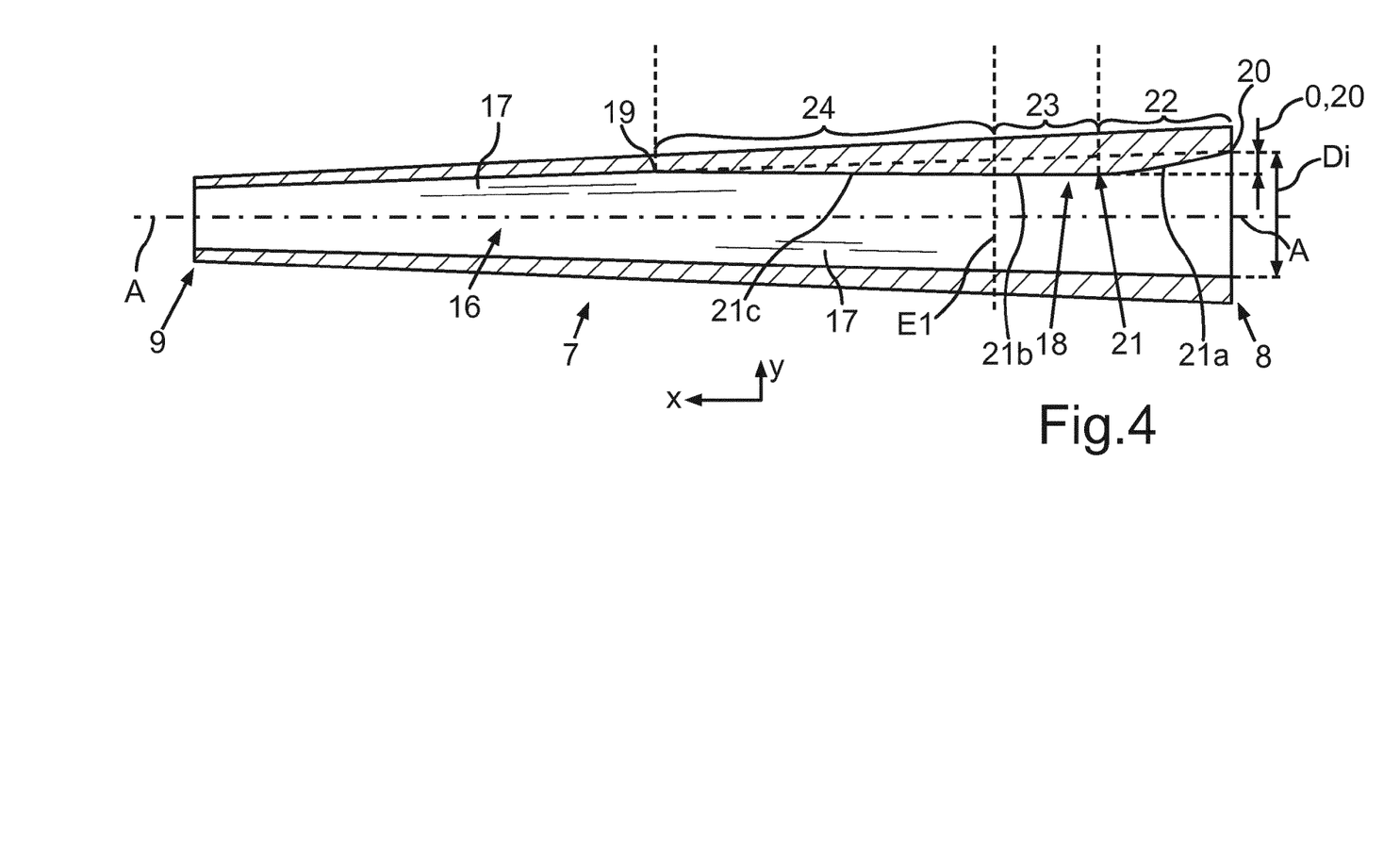
FIG. 4 a first longitudinal sectional view of the injector tip of the ocular lens injector device according to FIG. 1.

In FIG. 4 a first longitudinal sectional view of the injector tip 7 is shown, with the sectional plane being in the x-y plane. As can be seen, the injector tip 7 is of a design that tapers off towards the front end 9. The injector tip 7 comprises an injection duct 16, which is bounded by an inner wall 17. The wall thickness of the injector tip 7 in the embodiment continuously decreases from the rear end 8 towards the front end 9 and amounts to between 0.15 mm and 0.25 mm at the front end 9.

The injector tip 7 and thus also the injection duct 16 have a central longitudinal axis A, which extends in the x direction.

At the inner wall 17 an inwardly extending step 18 is formed. This discontinuity or step 18 serves for promoting the rolling-up of the intraocular lens 10 on the shifting path along the central longitudinal axis A in the injection duct 16.

As can be seen from the representation in FIG. 4, the step 18 extends only along part of the entire length (extension in the x direction) of the injector tip 7. In particular it is envisaged in the embodiment that a front end 19 of step 18 is formed spaced apart from the front end 9. The step 18 thus ends far from the front end 9. In the embodiment a rear end 20 of the step 18 is designed such that it coincides with the rear end 8 of the injector tip 7. It may, however, also be envisaged that the rear end 20 of the step 18 ends inwardly offset and spaced apart from the rear end 8 of the injector tip 7.

The step 18 is designed such that it has a crown line 21, which has a non-straight course. This means that the distance of the crown line 21 from the central longitudinal axis A along the length of the step 18 is varied and changed at least once.

In the embodiment it is provided that the step 18 has three sections, which are characterized by the course of their crown line sections. In this respect it is envisaged that the step 18 has a first section 22. In this section 22 a first crown line section 21a is formed, which starting from the rear end 20 of the step 18 rises at a sloping angle. This means that the distance of this first crown line section 21a starting from the rear end 20 to the central longitudinal axis A decreases, in particular decreases continuously. Directly adjacent to this first section 22 is formed a third section 23. In this third section 23 the crown line 21 has a third crown line section 21b, which extends in a straight line. This means that along the entire length of this third crown line section 21b the crown line 21 has a constant distance from the central longitudinal axis A.

Directly adjacent to this third section 23 is formed a second section 24 of the step 18. In this second section 24 the crown line 21 is formed with a second crown line section 21c, which in particular continuously falls at a sloping angle. Moreover, it is envisaged that in the third section 23 the step 18 has its maximum height and thus its maximum dimension between the inner wall 17 to the crown line 21 and thus to the third crown line section 21b. This distance is preferably between 0.15 mm and 0.3 mm, in the embodiment 0.2 mm.

Moreover, it can be seen that in the embodiment the length and thus the extension in the x direction of the third section 23 is shorter in comparison with the two other sections 22 and 24. Moreover, also the first section 22 is shorter than the second section 24.

The length of the third section 23 in the embodiment is 2 mm, wherein this is merely an example and in no way to be understood as restrictive. This length can also differ clearly.

Moreover, in FIG. 4 also the position of a plane E1, which extends in the y-z direction, is drawn. This plane E1 represents the plane, in which the edges 14 and 15 of the intraocular lens 10 during folding or rolling-up within the injector tip 7 come into physical contact whilst moving along the central longitudinal axis A.

Figure 5:
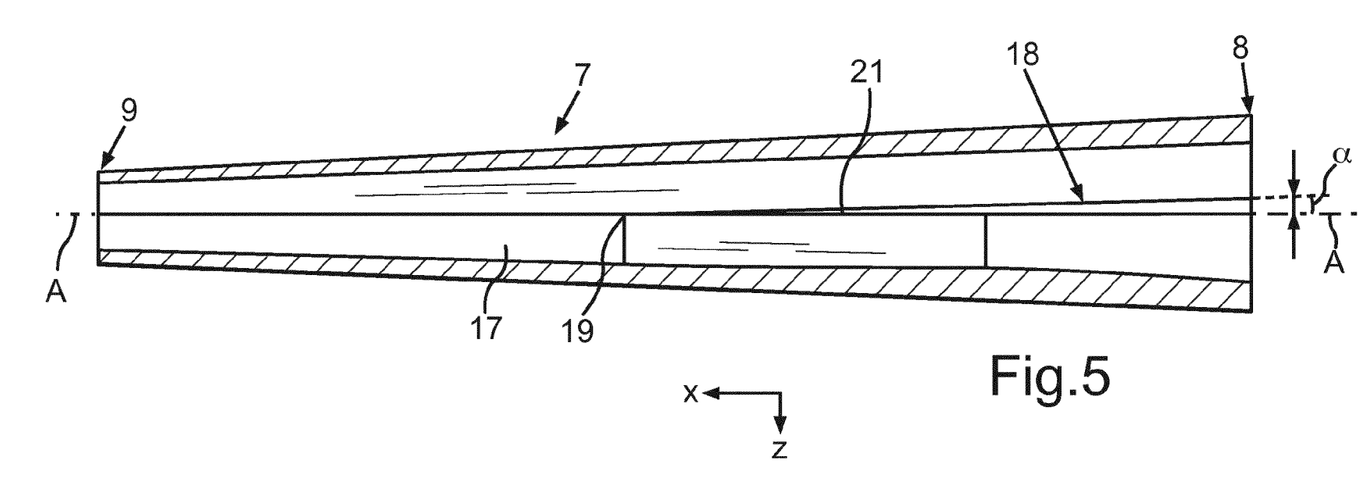
FIG. 5 a further longitudinal sectional view of the injector tip.

In FIG. 5 in a further longitudinal sectional view in the plane x-z the injector tip 7 is shown. In this embodiment thus quasi also the step 18 is viewed from a top perspective. In the embodiment it is provided that the step 18 relative to a vertical plane, which extends through the x-y plane, is inclined at an angle of >0° and <1°.

Figures 6, 7:
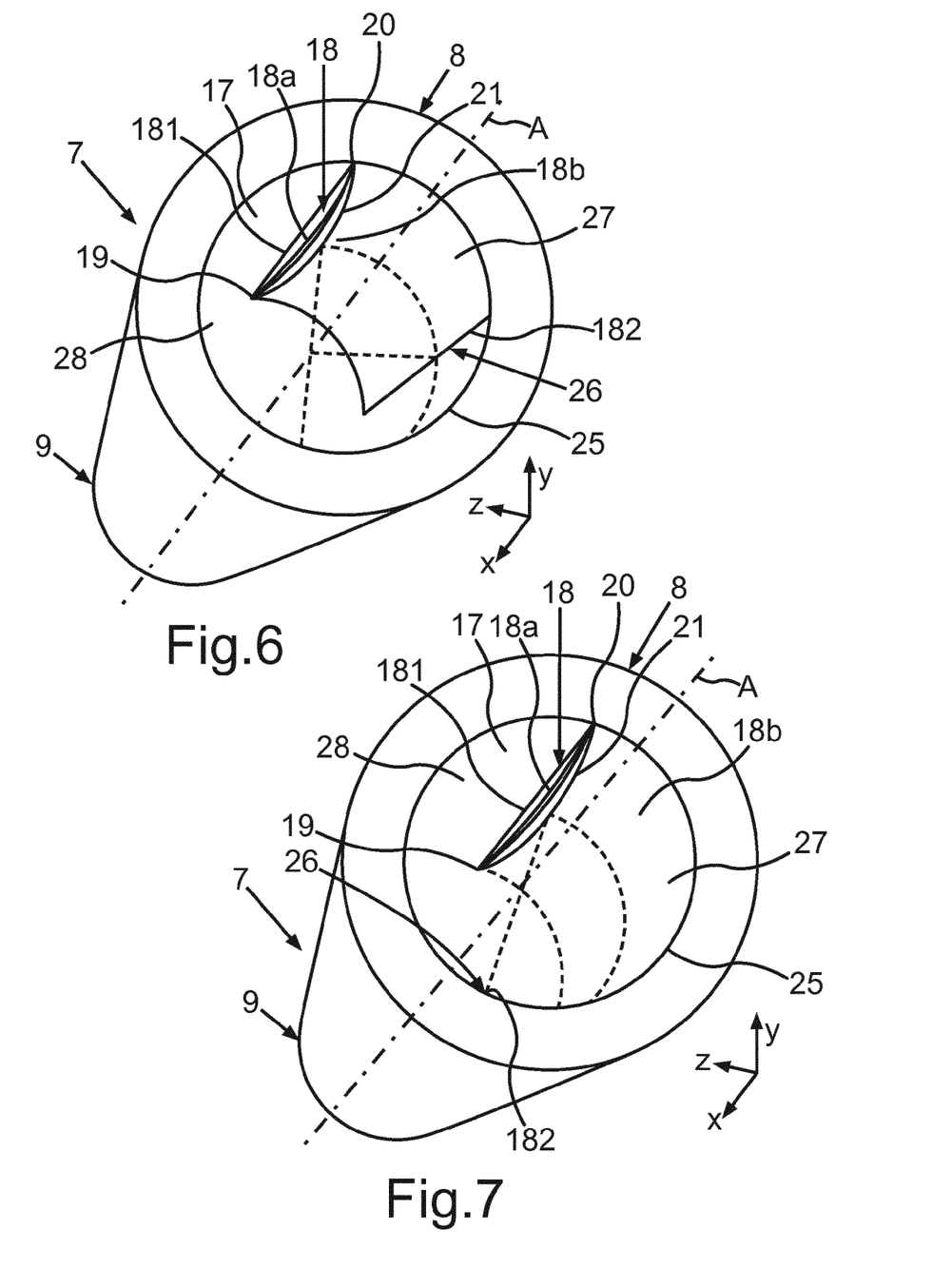
FIG. 6 a cross-sectional view of the injector tip according to FIG. 4 and FIG. 5.
FIG. 7 a cross-sectional view of the injector tip according to a further embodiment.

In FIG. 6 in a perspective view a first embodiment of the injector tip 7 is shown. In this embodiment it can be seen that the step 18 has a steep step flank 18a and a flat step flank 18b. The two step flanks 18a and 18b end in the crown line 21. On the other hand, the steep step flank 18a with a second step flank end 181 ends in the inner wall 17. As can be seen in the representation according to FIG. 8, the flat step flank 18b is designed such that it extends over about a quarter of the entire outline 25 of the inner wall 17 in the circulation direction viewed about the axis A. This means that the flat step flank 18b has its step flank end 182, which faces away from the crown line 21, at an inner wall place 26, wherein this inner wall place 26 is arranged offset at an angle of about 90° from the step 18, in particular the crown line 21. Through the flat step flank 18b thus a wall section 27 of the inner wall 17 is created, which extends or forms starting from the in circulation direction about the axis A starting from the step 18 at an angle of about 90°. In connection with the non-straight course of the crown line 21 this flat step flank 18d is formed as a curved surface, which moreover varies in height viewed in the direction of the axis A, such that a kind of single-wave profile is formed. By contrast, starting from the steep step flank 18a in the circulation direction about the axis A counter-clockwise a further wall section 28 is formed, which is equally dimensioned to reach up to the inner wall place 26. Starting from the step 18, in particular the steep step flank 18a and in particular the second step flank end 181, this further wall section 28 is thus dimensioned over an angle interval of essentially 270°. The outline 25 has a first radius, which is constant across this further wall section 28 and which moreover is even larger than a possible second radius, which is dimensioned to extend across a quarter circle of the first wall section 27.

In FIG. 7 in a perspective view a further embodiment of the injector tip 7 is shown. Unlike in the representation according to FIG. 6 here it is envisaged that the flat step flank 18b extends not only along essentially a quarter circle of the outline 25, but extends along essentially a half circle of the outline 25.

In the two embodiments according to FIG. 6 and FIG. 7 the shape design of the surface of the flat step flank 18b is similar to a riding saddle.

Figure 8:
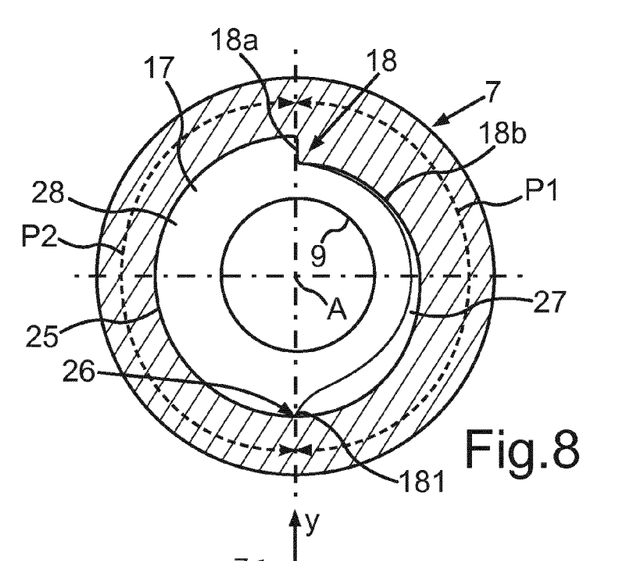
FIG. 8 a perspective view of the injector tip according to the embodiment in FIG. 7.

FIG. 8 shows in a cross-sectional view in the y-z plane the embodiment of the injector tip 7 according to FIG. 7. In this regard a cross-section in the area of the third section 23 is shown. With the sketched arc arrows P1 and P2 examples of the angle extension of the wall sections 27 and 28 are shown. In this connection also the extension of the flat step flank 18b in the circulation direction about the central longitudinal axis A is shown, which then, as has already been mentioned, ends with the step flank end 182. As already mentioned, the wall sections 27 and 28 end in the inner wall place 26 without forming any edges, and therein both share the same tangent equally resulting in a stepless transition.

Figure 9:
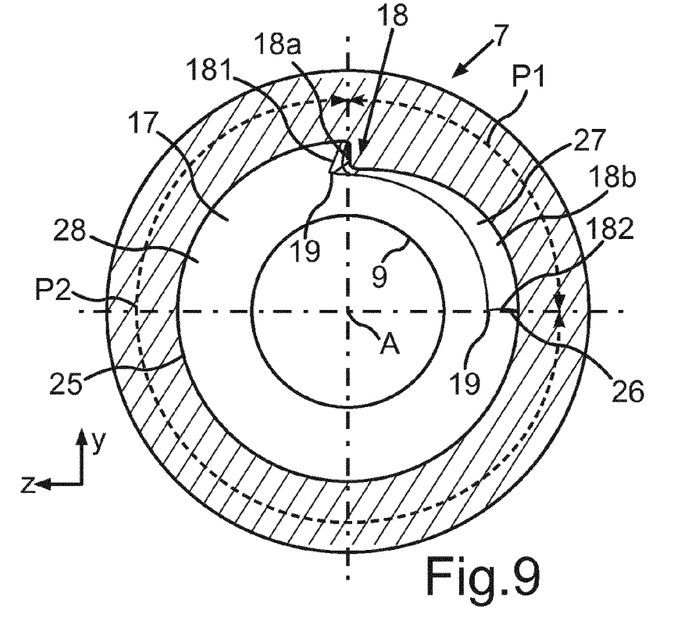
FIG. 9 a perspective view of the injector tip according to the embodiment in FIG. 6.

In FIG. 9 a cross-sectional view in the y-z plane of the injector tip 7 according to the embodiment in FIG. 6 is shown. Here, too, a cross-section at the level of the third section 23 is shown. Moreover, the representation in FIG. 9 is to be understood in analogy to that in FIG. 8.

As can be seen from the representations in FIGS. 4 to 9, the step 18 with regard to the position of the injector tip 7 at the injector tube 2 is in the 12 o'clock position.

Figure 10:
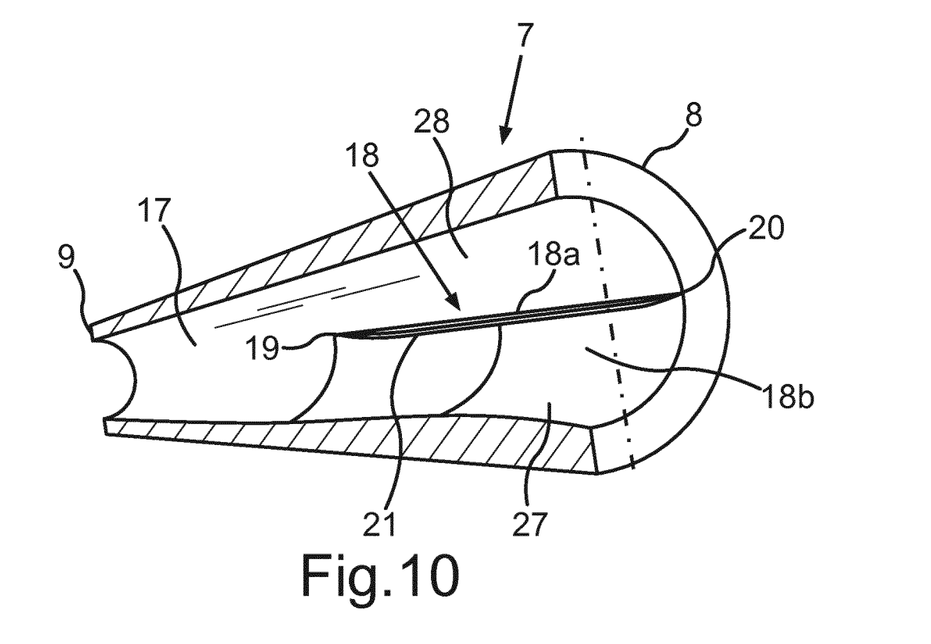
FIG. 10 a perspective longitudinal sectional view of the injector tip according to FIG. 9.

In FIG. 10 in a perspective longitudinal sectional view the injector tip 7 according to the embodiment in FIG. 7 and FIG. 8 is shown.

The invention claimed is:

1. An injector tip for an ocular lens injector device, the injector tip comprising a tapered injection duct having a front end and a rear end and being bounded by an inner wall, wherein at the inner wall an inwardly extending step is formed, and the step is formed only along part of an entire length between the front and the rear end of the injection duct and ends at a distance from the front end of the injection duct, wherein the step in a circulation direction about a central longitudinal axis of the injection duct has a steep step flank and a flat step flank, which converge at a crown line; and wherein the crown line has a gradually rising first crown line section and a gradually falling second crown line section; and wherein the crown line has a crown line section formed between the first and the second crown line sections and extending a constant distance from the central longitudinal axis.

2. The injector tip according to claim 1, wherein the step is formed to end in the rear end.

3. The injector tip according to claim 1, wherein the step at least along part of the entire length of its crown line has a non-straight course of the crown line.

4. The injector tip according to claim 3, wherein the crown line has a straight third crown line section.

5. The injector tip according to claim 4, wherein the third crown line section is formed between the first and the second crown line sections.

6. The injector tip according to claim 1, wherein the flat step flank has a curved outline, which extends starting from the crown line up to an inner wall place spaced in the circulation direction about the central longitudinal axis of the injection duct at an angle of between 70° and 190° from the step.

7. The injector tip according to claim 1, wherein the inner wall in a cross-section perpendicular to a central longitudinal axis of the injection duct has a wall section with a first radius, which extends from a first step flank end of the steep step flank of the step up to an inner wall place with the first radius, wherein the inner wall place starting from the crown line in the direction of the wall section is formed at an angle of between 150° to 290° at a distance from the step.

8. The injector tip according to claim 7, wherein the inner wall place starting from the crown line in the direction of the wall section is positioned at an angle of between 170° to 190° or at an angle of between 260° and 280° at distance therefrom.

9. The injector tip according to claim 7, wherein the wall section and a second wall section formed by the flat step flank both end at the inner wall place and there share the same tangent.

10. The injector tip according to claim 7, wherein the inner wall place starting from the crown line in the direction of the wall section is formed at an angle of between 170° and 280° at a distance from the step.

11. The injector tip according to claim 1, wherein the position of a maximum height of the crown line of the step in the direction of the central longitudinal axis starting from the rear end of the injection duct is determined in dependency on an inner diameter Di of the injection duct and the diameter DO of an optical element of an intraocular lens, which is to be slid through the injector tip, and the thickness E0 of this intraocular lens at an edge, wherein $Di=(1/\pi)*D0+E0$.

12. The injector tip according to claim 11, wherein the maximum height of the crown line is between $0.5*E0$ and E0.

13. The injector tip according to claim 1, wherein the step is arranged at an angle of between 0° and 1° relative to a vertical axis of the injection duct which intersects the central longitudinal axis of the injection duct.

14. A device comprising an injector tip according to claim 1 and an ocular lens.

15. An ocular lens injector device comprising an injector tip according to claim 1.

\* \* \* \* \*